(12) United States Patent
Pérez

(10) Patent No.: US 8,684,028 B2
(45) Date of Patent: Apr. 1, 2014

(54) FUEL QUALITY TRACEABLE AND REMOTE SYSTEM

(75) Inventor: Camilo Vazquez Pérez, Arteixo (ES)

(73) Assignee: Pecofacet (US), Inc., Mineral Wells, TX (US)

( * ) Notice: Subject to any disclaimer, the term of this patent is extended or adjusted under 35 U.S.C. 154(b) by 302 days.

(21) Appl. No.: 13/056,190

(22) PCT Filed: Jul. 31, 2008

(86) PCT No.: PCT/IB2008/002013
§ 371 (c)(1),
(2), (4) Date: Jan. 27, 2011

(87) PCT Pub. No.: WO2010/013084
PCT Pub. Date: Feb. 4, 2010

(65) Prior Publication Data
US 2011/0130882 A1    Jun. 2, 2011

(51) Int. Cl.
*F16K 31/02* (2006.01)
(52) U.S. Cl.
USPC ............ 137/487.5; 137/485; 137/488; 137/2; 141/192
(58) Field of Classification Search
USPC ................... 137/2, 485, 487.5, 488; 141/192
See application file for complete search history.

(56) References Cited

U.S. PATENT DOCUMENTS

| | | | |
|---|---|---|---|
| 2,896,502 A | 7/1959 | Nordin | |
| 3,794,909 A | 2/1974 | Smith | |
| 3,941,479 A | 3/1976 | Whitehead | |
| 4,140,005 A | 2/1979 | Kittelson | |
| 4,413,533 A | 11/1983 | Diesel | |
| 4,518,955 A * | 5/1985 | Meyer | 340/605 |
| 4,809,543 A | 3/1989 | Baillie | |
| 5,040,890 A | 8/1991 | North, Jr. | |
| 5,126,934 A * | 6/1992 | MacFadyen | 700/11 |
| 5,148,945 A | 9/1992 | Geatz | |

(Continued)

FOREIGN PATENT DOCUMENTS

| | | |
|---|---|---|
| JP | 2001027599 | 1/2001 |
| JP | 2005181120 | 7/2005 |

(Continued)

OTHER PUBLICATIONS

Document 1, HAIC PM 4000 Operator Manual, Dec. 2007, edition 5.*

(Continued)

*Primary Examiner* — Eric Keasel
*Assistant Examiner* — Minh Le
(74) *Attorney, Agent, or Firm* — Greenberg Traurig, LLP; Chinh H. Pham

(57) ABSTRACT

A fuel quality traceable and remote system for monitoring and controlling fuel characteristics during transport from a fuel supply to a supplied device is provided. The system includes one or more subsystems that include at least one sensor monitoring the characteristics of the fuel. The sensor operably sends the data relating to the characteristics to a data register-transmitter which sends the data to a base station that uploads the data to a remote server. The remote server is remotely accessible by a user. The system can also generate warning messages to warn a user when the characteristics are outside a tolerable range. Further, the system can automatically or manually interrupt fuel transport when the characteristics are outside a tolerable range.

19 Claims, 2 Drawing Sheets

(56) References Cited

U.S. PATENT DOCUMENTS

| | | | |
|---|---|---|---|
| 5,209,275 A * | 5/1993 | Akiba et al. | 141/83 |
| 5,537,879 A | 7/1996 | Malczewski et al. | |
| 5,568,825 A * | 10/1996 | Faulk | 137/624.11 |
| 5,751,422 A | 5/1998 | Mitchell | |
| 5,893,388 A * | 4/1999 | Luker | 137/456 |
| 5,894,080 A | 4/1999 | Dybdahl | |
| 6,062,092 A | 5/2000 | Weaver | |
| 6,168,647 B1 | 1/2001 | Perry, Jr. et al. | |
| 6,357,304 B1 | 3/2002 | Mayeaux | |
| 6,584,865 B1 | 7/2003 | Doherty et al. | |
| 6,813,303 B2 | 11/2004 | Matsuda et al. | |
| 6,843,103 B2 | 1/2005 | Aguilera et al. | |
| 7,024,867 B2 | 4/2006 | Arman et al. | |
| 7,412,994 B2 * | 8/2008 | Corless et al. | 141/198 |
| 7,518,719 B2 | 4/2009 | Sprenger et al. | |
| 7,642,742 B2 | 1/2010 | Curello et al. | |
| 7,854,158 B2 | 12/2010 | Burns et al. | |
| 7,948,621 B2 | 5/2011 | Burns et al. | |
| 2002/0007858 A1 | 1/2002 | Xu et al. | |
| 2003/0131904 A1 | 7/2003 | Dodson | |
| 2003/0235926 A1 | 12/2003 | Knollenberg et al. | |
| 2004/0079236 A1 | 4/2004 | Welker | |
| 2004/0139785 A1 | 7/2004 | Abdul-Khalek | |
| 2005/0151968 A1 | 7/2005 | Drake et al. | |
| 2008/0156073 A1 | 7/2008 | Burns et al. | |
| 2008/0230146 A1 | 9/2008 | Kastner et al. | |
| 2011/0061740 A1 * | 3/2011 | Watkins | 137/2 |

FOREIGN PATENT DOCUMENTS

| | | |
|---|---|---|
| WO | WO 03/046688 | 6/2003 |
| WO | WO 2007/019106 | 2/2007 |
| WO | WO 2008/089259 | 7/2008 |

OTHER PUBLICATIONS

Office Action in Chinese Application No. 200880130607.4 mailed Sep. 6, 2012.
English translation of the Search Report conducted for Application in U.S. Appl. No. 13/056,190.
Facet International, "Online Particle Detector: Facet iCount," Facet International, pp. 1-8 (2010).
Office Action in U.S. Appl. No. 11/823,585 mailed Nov. 4, 2010.
Office Action cited in U.S. Appl. No. 11/823,585 mailed Oct. 30, 2009.
Office Action cited in U.S. Appl. No. 11/823,585 mailed Jun. 14, 2010.
Office Action cited in U.S. Appl. No. 11/646,846 mailed Sep. 23, 2008.
Office Action cited in U.S. Appl. No. 11/646,846 mailed Apr. 29, 2009.
Office Action cited in U.S. Appl. No. 11/646,846 mailed Mar. 10, 2010.
International Search Report based on International Application No. PCT/US2006/049429 mailed Feb. 15, 2008.
International Search Report based on International Application No. PCT/US2007/015138 mailed May 29, 2008.
International Search Report based on International Application No. PCT/IB2008/002013 mailed Mar. 26, 2009.
Japanese Office Action cited in Japanese Application No. 2010-514718 mailed Apr. 10, 2012.
"HIAC PM4000, On-line Laser Particle Monitor Operator Manual: 2.1 PT4000 Overview," RPS. Ed. 5. pp. 13-14 (2007).
Written Opinion cited in Singapore Application No. 201100376-1 mailed Apr. 5, 2012.

* cited by examiner

FUEL QUALITY TRACEABLE AND REMOTE SYSTEM

CROSS REFERENCE TO RELATED APPLICATIONS

This application is a national phase filing under 35 U.S.C. 0371 of International Application No. PCT/IB2008/002013, filed on Jul. 31, 2008, the disclosures of which is hereby incorporated herein by reference in its entirety.

This invention relates to a fuel quality monitoring and control system whose aim is to provide control and quality monitoring of fuel during fuel handling operations, such as during aircraft refueling, fuel storage terminals, fuel analysis in pipelines or hydrant systems, or others. This invention can be also applicable in general to any other type of fluids (e.g. diesel oil or oils) and installations that imply the transfer and/or storage of the aforementioned fluids.

BACKGROUNDS OF THE INVENTION

During refueling operations, the fuel is filtered by a filter/water separator or a monitor filter. The quality of fuel that is being supplied to aircrafts must fulfill the intoplane quality standards, and therefore fuel-cleanliness management and measurement becomes necessary. On the other hand, in fuel storage terminals and pipelines, monitoring the particulate matter and free water content in fuel is also desired as fuel quality can effect the overall performance of or result in wear or damage to down stream systems that use the fuel; therefore measurement of particulate matter and free water is required during fuel handling operations.

Conventionally, the aforementioned measurements are made manually in situ that is in the place of application, though without having any control of the quality of the fuel intoplane, or other device, or acquiring records of the fuel quality continuously. This fact produces objections due to the difficult administration and monitoring of the required operations. Typically, the measurements must be performed on fuel that is removed from the flow of fuel into the supplied device. However, this fuel cannot then be added back into the flow of fuel and must be discarded, which results in a significant and costly loss of fuel. In many instances, the fuel must be shipped to off-site facilities for testing, which results in significant delays in determining the fuel quality, even to the extent that the fuel is consumed prior to acquiring the testing results. As such, when problems in the quality of the fuel are detected, only manual flow control systems can be actuated.

The current state-of-the art does not include any fuel quality control system that enables monitoring and management of fuel handling operations that allow the storage and monitoring of data within a plurality of subsystems.

The present invention provides improvements over the current state of the art and provides a monitoring and control system that may be completely unattended and allows for automatic fuel quality monitoring from a local and/or remote site without the requirement of an operator's intervention and which may automatically control the fuel flow based on the quality of the fuel.

DESCRIPTION OF THE INVENTION

In order to achieve the objectives and to avoid the above objections, embodiments of the invention include a fuel quality control system that is applied to one or more combined or independent subsystems. Each of the subsystems includes at least a fuel supplier element to supply a fuel tank or device to be fed through a fuel supply system (hose, pipe or similar device) that includes an electronic sensor capable of detecting free water and/or particulate matter. The subsystems may also include a flow sensor for detecting a flow of fluid through the system and for starting/stopping the gathering of data.

An embodiment of a system according to the invention measures the free water and/or particulate matter contamination level. The system may also monitor and measure other parameters utilized in other applications and provides a local registration of the gathered data. The gathered data is subsequently delivered through the internet or other data network to facilitate continuous data storage and monitoring. This data may then be further remotely accessed by users. Furthermore, the system enables the automatic interruption of the fuel supply when predetermined parameters, such a fuel quality, are not observed. As such, the subsystems may include a flow switch, or other flow control device, for controlling the flow of fuel through the fuel supply system that can be used to automatically or manually interrupt flow of fuel when poor fuel quality is sensed.

According to an embodiment of the present invention, the data gathered corresponding to the electronic sensor and, where appropriate, the data corresponding to the several parameters such as the, fuel quality, differential pressure across the filter, density, temperature, etc. are transferred to a data register-transmitter device that is connected to a data insert block within a data network. The data register-transmitter device transmits the data to a remote server that registers and stores the data and, at the same time, enables remote monitoring of the same. The data register-transmitter device and/or server is also connected to a warning sending block. Thereby, any authorized user of the system receives warnings in anomalous situations (email, SMS or others) and may consult those data through a computer connected to the aforementioned data network.

The referred electronic sensor can be a laser particle counter that is capable of detecting free water and/or particulate matter in fuel.

In a preferred embodiment of this invention, the connection between the data register-transmitter block and the data insert block can be carried out through a cable connection, through a wireless system such as by a radio waves system, or through both.

As the subsystems may be utilized in remote areas where power may not be easily accessed, the data register-transmitter may be powered by photovoltaic solar energy panels.

Taking into account the structure described above, embodiments of the system of the invention have one or more of the following advantages:

It automatically initiates gathering of data through a flow detection signal.

It facilitates quality monitoring and management of fuel handling operations.

It enables the user to access the data gathered from the monitoring remotely or locally.

It provides information about the differential pressure of the filter/water separator or monitor filter that is used in certain applications; and/or about other parameters such as particulate matter and free water, density, temperature.

It enables graphic visualizations of the content of particulate matter and/or free water, which may be exportable to MSExcel® format or in other embodiments to other spreadsheet formats.

It facilitates generating personalized reports to the associated users; these personalized reports may be provided in PDF format or other useable formats.

It enables a local storage capacity over 17,000 fueling operations.

It enables alarms through email, SMS and/or other messaging means.

It enables the interruption of fuel supply in case of sensed poor fuel quality or alarm.

It enables storage of the data obtained in each fuel handling operation for an undefined period of time in the data storage server.

It can use parameterizations in agreement to international fuel handling regulations.

Other embodiments and features of the invention will become more apparent from the following detailed description when taken in conjunction with the accompanying drawings.

BRIEF DESCRIPTION OF THE FIGURES

Other embodiments of the invention will become more apparent from the following detailed description when taken in conjunction with the accompanying drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DESCRIPTION

An Example of the Achievement of the Invention

Figure 1:
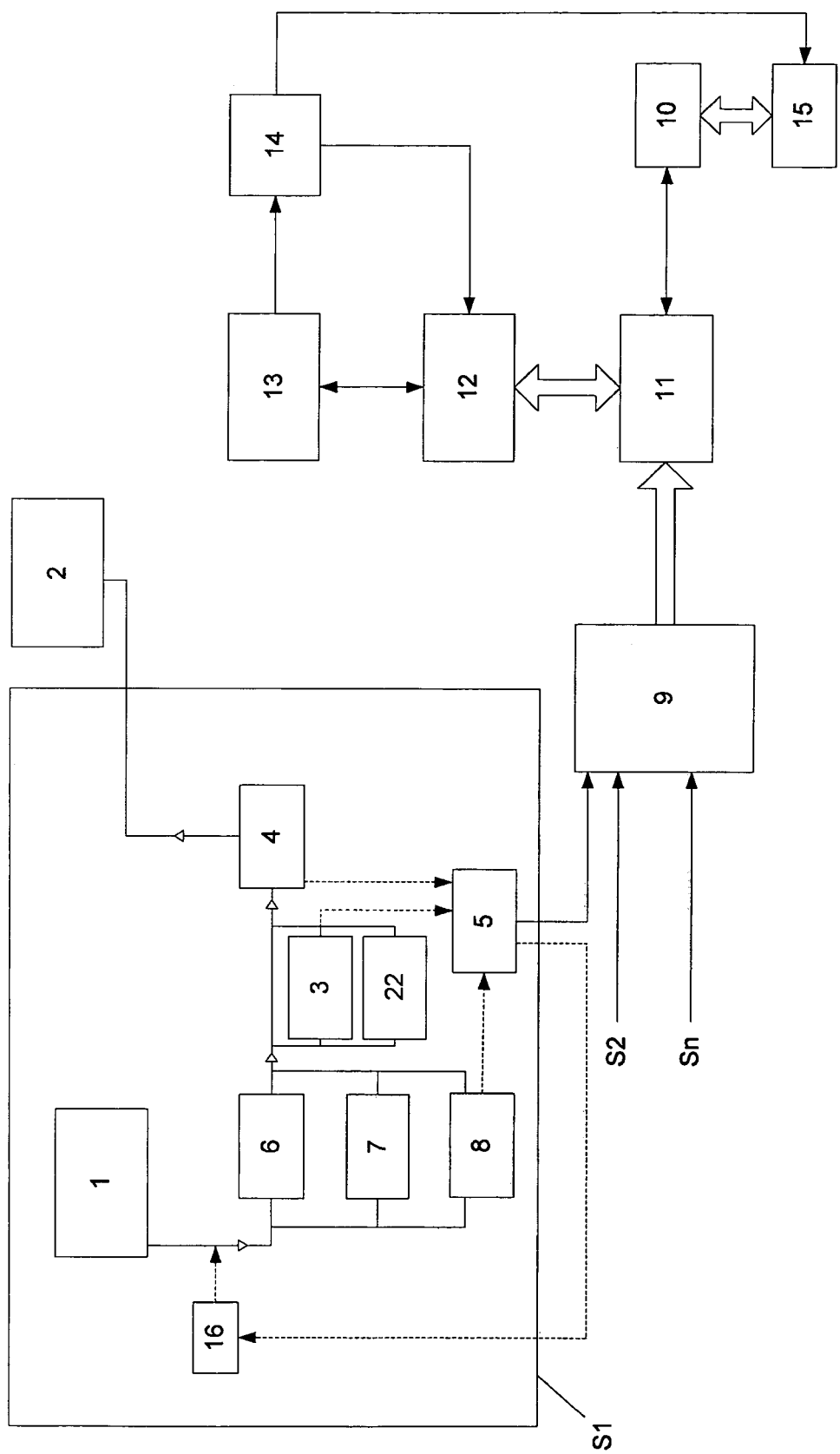
FIG. 1 schematically depicts a fuel control and monitoring system in block diagram format carried out according to embodiments of this invention.
Figure 2:
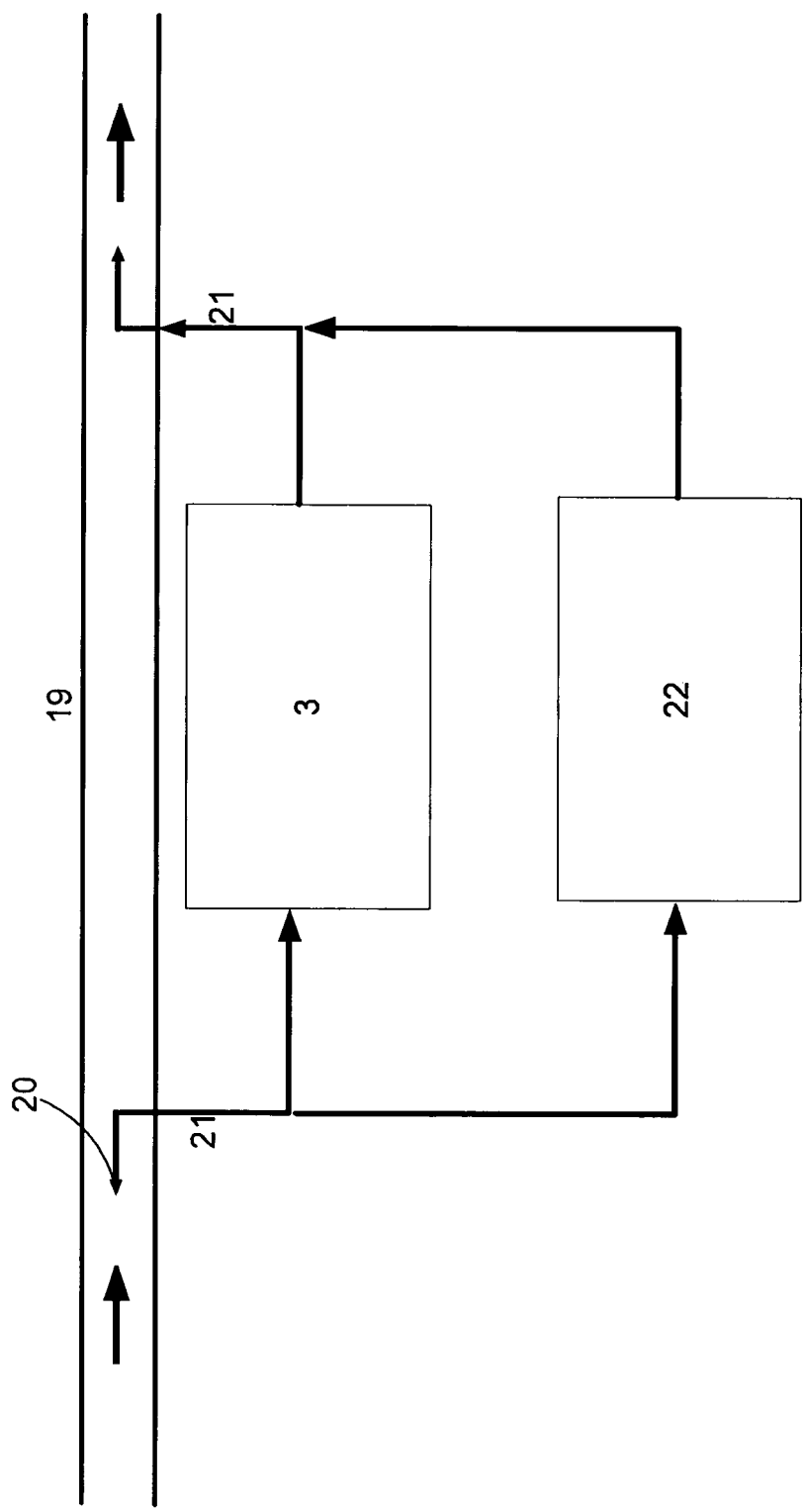
FIG. 2 is a simplified schematic illustration of the sensors arranged in parallel with the primary fuel flow of the fuel quality traceable and remote system of FIG. 1.

Next, a description of an example of the invention is carried out referring to the numbering adopted in FIGS. 1 and 2.

A fuel quality traceable and remote system, of this example is schematically illustrated in FIG. 1 through some functional blocks. The system may include one or more fuel supply subsystems (S1, S2, ... Sn) that can be combined among them to form a network of fuel delivery systems, or be independent. These subsystems (S1, S2, ... Sn) are typically fuel handling systems that may be pipeline systems, fuel truck systems, or other fuel delivery or handling systems.

Generally, each subsystem includes fuel supplier element (1) for supplying fuel to a tank or a supplied device (2) through a fuel pipes system, such as a hose, pipe or analogous fluid handling device. The fuel supplier element (1) may be, for example and without limitation, a fuel truck, a fuel storage tank, a fuel pipeline or other device for supplying fuel to a supplied device (2)

The supplied device (2) is most typically a device that utilizes the fuel such as an aircraft or other engine powered device. However, the supplied device (2) could also be a further onsite storage device such as a further temporary fuel storage tank.

It should be noted that while one preferred implementation of this system is at airports and for use with refueling aircraft, the system could be implemented in any fuel handling system where it is desirable to monitor the characteristics of fuel that is being transferred between two storage locations. For example, the monitoring system could be used at a local construction site where the fuel being added to the construction equipment from a tanker truck or onsite storage tank is monitored for quality and characteristics.

The subsystem (S1) further includes a sensor (3), which may be a single sensor device for monitoring the fuel characteristics as the fuel flows from the fuel supplier (1) to the supplied device (2). However, a bank of sensors may be used, such as illustrated in FIG. 2 (i.e. sensors (3) and (22) to monitor the various characteristics of the fuel.

In a preferred embodiment, electronic sensor (3) is capable of detecting free water and/or particulate matter, which may be referred to generally as contaminant particles. The subsystem may further include a flow control device (4), situated downstream from the sensor (3) in order to avoid any distortion of the sample, for controlling the flow of fuel from the fuel supplier (1) to the supplied device (2) in the event that substandard fuel quality is detected. Furthermore, in certain applications an inline filter (6) can be included to filter the fuel prior to being supplied to supplied device (2), as it is represented in the subsystem S1 of the FIG. 1.

As fuel is transferred from the fuel supplier element (1) to the supplied device (2) through the pipes, the fuel, or a sample of the fuel (as illustrated in FIG. 2), passes through the sensor (3) that monitors the free water and/or particulate matter within the fuel. A sample of the fuel also passes through density and temperature sensor (22) to monitor these additional characteristics of the fuel.

When a filter (6) is present in the flow path from the fuel supplier (1) to the supplied device (2), it is preferred to have the sensors (3), (22) downstream from the filter (6) so as to monitor the fuel in a state most closely representing its state as it is supplied to supplied device (2). Further, this orientation allows the sensors (3), (22) to be used as a monitor of the quality and condition of the filter (6).

With additional reference to FIG. 2, in the illustrated embodiment, sensors (3), (22) are positioned, preferably, in parallel with the primary fuel flow, which is identified by reference numeral (19). More particularly, the sensors (3), (22) only test samples of the fuel flows to the supplied device (2) rather than the entire fuel flow.

A pitot tube (20), or similar device for separating a sample of fluid from a fluid flow, separates off a sample portion (21) of the primary fuel flow (19) to be tested by sensors (3), (22). Preferably, the pitot tube (20) is positioned proximate the center of the primary fuel flow (19) to acquire the most common sample of fuel.

Once separated from the primary fuel flow (19), parts of the sample portion (21) passes through sensors (3), (22) to test the quantity of particulate and/or free water present in the sample portion (21) as well as the temperature and density of the fuel. This sample portion (21) then passes back into the primary fuel flow (19) and is entrained therein.

One major benefit of this method of testing is that the sample portion (21) of fuel is not discarded or wasted due to testing, such as in the past when discrete samples of fuel were extracted from the fuel being transferred to supplied device (2) and then physically tested and then discarded.

However, in alternative embodiments, a sensor (3) may be inline with the primary fuel flow (19) such that the entire flow of fuel is monitored.

Further, in less-desirable alternative embodiments, the fuel may be sampled and tested and then discarded without being returned back to the primary fuel flow (19). While this embodiment may not have the benefit of preventing waste, it can still include some of the benefits of real-time monitoring and control of the fuel flow more fully outlined below.

In a preferred embodiment, sensor (3) utilizes a laser counter for detecting the presence of particulate matter and/or free water. The laser counter can be configured to utilize different channels for detecting and counting the number of particles in different particle size ranges. In a preferred implementation, the laser counter utilizes shadow counting methods for detecting the presence of and monitoring the quantity of particulate and/or free water in the fuel. A light source, typically a laser, will pass a beam of light through the sample of fluid. As the light passes through the fluid, any contaminate particles will generate shadows that then can be sensed by a photosensor which will convert the shadows into an electrical signal that can be monitored and analyzed to ultimately determine the contaminate particle concentration.

However, in alternative methods, the sensor (3) could utilize light scattering methods for detecting the presence and monitoring the quantity of particulate and/or free water in the fuel.

Other parameters that may be monitored in addition to the ones monitored by sensor (3) may include the density and the temperature of the fluid by a density and temperature sensor (22), the pressure drop of the fluid across the filter (6), etc.

The data obtained during the fuel transfer corresponding to electronic sensors (3), (8) and (22) are transferred to a data register-transmitter device (5). Typically, each subsystem S1-SN will include a dedicated local data register-transmitter device (5). In other words, for example, each fuel truck or each fuel supply tank will have its own sensors (3) and (22) and its own data register-transmitter device (5).

While illustrated as a separate component coupled to sensors (3) and (22), the data register-transmitter device (5) could be formed as a single component with sensors (3) and (22).

The data register-transmitter device (5) of an individual subsystem is typically a data processor device that includes memory and records and stores the data gathered by sensors (3), (8) and (22) locally for that subsystem and then makes a subsequent transmission of a packet or packets of information for each operation cycle to a data insert block (9) or base station. Depending on the embodiment, the data register-transmitter device (5) may also convert the raw data gathered by or signals sent by sensors (3), (8) and (22) into useable data such as, for example, density, temperature, contaminant particle content, etc., prior to transmitting the information to the data insert block (9) or base station. However, alternatively, the data register-transmitter device (5) could directly send the output of the sensors to the data insert block (9) or base station such that the data from sensors (3), (8), (22) is then processed into useable information by another device.

As used herein, an operation cycle (e.g. during fueling or transferring) will be the beginning and stoppage of fuel flow, whether or not the supplied device has actually been filled. For example, if the fuel flow is accidentally stopped prematurely and then restarted to finish filling the supplied device (2), this will consist of two operation cycles.

Typically, but not mandatory, each subsystem (S1, S2, . . . Sn) can include a flow sensor device, that initiates data capture by the different sensors and devices such as the sensor (3), the density and temperature sensor (22), the differential pressure transmitter (8), when fluid flow is sensed and stops gathering data when fluid flow ceases.

As such, the sensors (3), (8) and (22) will continuously monitor the characteristics of the fuel flow throughout the entire operation cycle. Thus, a plot of the characteristics of the fuel over time can be generated to illustrate the fuel quality throughout the entire operation cycle. This is an added benefit over prior art monitoring systems where a single large sample was taken during each operation cycle. For example, if the fuel quality/characteristics vary throughout the operation cycle, the present system will be able to monitor the changes. However, in previous systems, if the quality of the fuel sample that was taken was within tolerable ranges, such as for example if it was taken from the top of a tank, but the fuel quality changed to being outside of tolerable ranges later in the fueling operation, for example, if the fuel was taken from the bottom of the tank where particulates had settled, the previous systems would never have caught the change in quality because, typically, only a single sample was taken.

As used herein, continuously monitoring the characteristics of the fuel flow encompasses minor time intervals between recording/monitoring the fuel characteristics. Minor time intervals may include, for example, one minute between capturing or monitoring fuel characteristics, but is preferably less than fifteen seconds between captures.

The data insert block (9) or base station is configured to connect to the internet or other data network and send the data through the internet or other data network (11) to a server (12).

The server (12) provides several features. In some implementations, server (12) governs an alarm control block (13), and a warning sending block (14), as illustrated in FIG. 1.

With this configuration, the alarm control block (13), being a or part of a data processor, can determine if the fuel being supplied to the supplied device (2) is outside of the desired standards and determine that a warning needs to be sent to an authorized user (15). The warning sending block (14) can then generate and dispatch the warning message to the authorized user (15). The warning sending block (14) can be configured such that warnings can be sent in anomalous situations by email, sms (short message service communications protocol providing text messages to mobile devices such as telephones) or other message protocol sent from the warning sending block (14) over wired or wireless communication channels.

Further, the server (12) permits an authorized user (15) connected to the data network or internet (11) to access the server (12) remotely to consult data about fuel transfers through a computer (10). Typically, the user (15) will access the server (12) through a secure website or network access interface. Through the interface, the user (15) can access the fuel transfer data for all of the subsystems S1-Sn for a given location such as, and not limited to, a particular airport, storage tank farm, etc. However, the user would not have access to other companies' information that may be stored on the server. As used herein, the server may be a single server or a bank of servers that are operably coupled.

The fuel transfer data relating to the particulate matter and/or free water content throughout a fuel transfer process can be displayed graphically to the user so that the user can analyze the fuel quality throughout the entire fuel operation cycle. In one implementation, the graphical representation may simultaneously provide the content of different sized particulate matter and/or free water, density, temperature, differential pressure across the filter, etc.

The fuel transfer data may include identifiers that identify the fuel supply device providing the fuel, the time and/or length of the fuel operation cycle, the load number and other information to identify the operation cycle so that the user (15) can analyze where the fuel came from or where the fuel was being supplied (i.e. which supplied device (2) received that batch of fuel).

The data register-transmitter device (5) can act by means of a control signal (16) over a deadman circuit depending on monitored parameters. As such, the data register-transmitter device (5) can act to cause a deadman circuit to automatically close and stop fuel flow into the supplied device (2) upon sensing of fuel quality or fuel flow outside a desired range.

This is possible as in some implementations, the data register-transmitter device (5) is a data processor that compare the information sent from sensors (3), (8) and (22) with predetermined tolerable ranges.

Typically, the deadman circuit will be provided a permanent signal, which may be a constant signal or no signal at all, during fueling of the supplied device (2) while the fuel is within a tolerable quality range. Once the sensor (3) or data register-transmitter device (5) determines that the fuel quality is outside of a tolerable range, an error or fault will be determined and the control signal (16) to the deadman circuit will be changed or stopped causing the deadman circuit to close and stop fuel flow to the supplied device (2).

As illustrated, the control signal (16) to the deadman circuit acts at an upstream location such as proximate or at the fuel supplying device (1) to stop fuel flow.

At the time fuel flow is stopped, the data register-transmitter device (5) shows a luminous sign, warning the user locally. Additionally or alternatively, the transmitter device (5) could activate an audible alarm warning the user locally.

Once the data reaches the server (12), this will govern the alarm control block (13) and the warning sending block (14) and, depending on the configuration, the warning sending block (14) may send a warning message to the authorized users (15).

The deadman arrangement will override any contrary control by the onsite operator who is distributing the fuel to the supplied device (2). Because the fuel operation cycle is terminated by operating the deadman circuit in the event of an error or fault, the data register-transmitter device (5) may be triggered to transmit information to the server (12).

Depending on the configuration, the data register-transmitter device (5) may transmit the packaged information including only sensed data, such as data from sensors (3), (8) and (22), only a warning signal such that the server (12) can send a warning message to the user (15), or a combination thereof. If the data register-transmitter device (5) only sends the data from sensor (3), the server or alarm control block (13) can be configured to further analyze the data to determine if an error message needs to be sent to the user (15).

In a similar way to the control signal (16) to the deadman circuit, any other device aimed to stop the flow can be controlled, such as: automatic valves, fueling pumps, etc.

The fuel parameters that the data register-transmitter device (5) or alarm control block (13) uses to determine whether to maintain and interrupt the fuel supply can be adapted to the International Fuel Quality Regulations. Specifically, this example has been developed according to the regulation API/IP1598.

In the illustrated example, the filter (6) of the subsystem S1 is a filter/water separator or a monitor filter, in which the data related to the pressure at the inlet and outlet are obtained through a differential pressure gauge (7) that is connected to the inlet and outlet in parallel with the filter (6), as well as to a differential pressure transmitter (8). This transmitter is at the same time connected to the data register-transmitter device (5). This filter (6) is normally used in subsystems such as the ones corresponding to aircraft refueling operations.

In a preferred implementation, the sensors (3) and (22), differential pressure transmitter (8) and/or data register-transmitter block (5) can be powered by a photovoltaic solar energy panel so that the system can be operated at remote locations. However, any other kind of power supply is obviously possible.

One or more of the subsystems S1, S2 . . . Sn can be a refueling system for aircrafts, where the fuel is filtered through a separator filter or a monitor filter prior to being added to the aircrafts; and where the fuel quality has to observe predetermined quality standards, such as those of API/IP1598 or intoplane. In this case, the level of contamination of solids and water, and optionally the differential pressure of the separator filter or monitor filter, are measured.

Other of the mentioned subsystems can be the terminal of fuel storage, where the fuel coming from the pipeline or from other means is analyzed. This can be used to help analyze the amount of filtration needed. Further, by monitoring the fuel as it is first delivered from a fuel source, i.e. from the pipeline, any potential areas of contamination that are present in the onsite fuel handling system after initial fuel delivery can be determined.

The corresponding sensor is set in the inlet of the installations and records the data referred to the content of solids and water in fuel.

Another of the subsystems mentioned, can be a pipeline or a moisturize system, where the analyzer is situated in the inlet of the moisturizer or in the outlet of the pipeline; and records the data about solids content in fuel.

The data insert block (9) can centralize uploading all of the information from all the subsystems to the server (12). It can be set up in the central offices of the company that utilizes the system of this invention.

Each company associated can exclusively access their own reports having also the possibility to download them through internet, connecting to a website. However, each company would not have access to other companies' data.

In further implementations, where it is not desirous to communicate the information to a remote server, the server or similar electronic device could be located locally with the subsystem (S1-Sn) such that the data can be analyzed on site. Further, the data insert block (9) could provide access to the data for a local user.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A fuel monitoring system comprising: one or more fuel supply subsystems (S1, S2, . . . Sn), each subsystem including:
   a fuel supplier (1);
   one or more sensors (3), (22), (8) for monitoring fuel characteristics of a flow of fuel supplied by the fuel supplier (1);
   a deadman circuit at an upstream location proximate to the fuel supplier that can act to stop the flow of fuel from the fuel supplier upon sensing of fuel characteristics outside a predetermined range;
   a signal, once communicated to the deadman circuit, that can override contrary control by an operator;
   a data register-transmitter device (5) for gathering data from the one or more sensors (3), (22), (7), the data register-transmitter device (5) is in operable communication with the one or more sensors (3), (22), (8);
   a server arrangement (12) for storing the data from the one or more sensors (3), (22), (8); and
   a data insert block (9) or base station for transmitting the data to the server arrangement (12), the base station (9) being in operable communication with the data register-transmitter device (5) for acquiring the data from the data register-transmitter (5) that is transmitted to the server arrangement (12).

2. The fuel monitoring system of claim 1, further comprising a flow switch or other flow control device (4) for controlling the flow of fuel from the fuel supplier (1).

3. The fuel monitoring system of claim 1, further includes a control signal (16) to the deadman circuit that operably stops the flow of fuel from the fuel supplier (1) upon the sensing of the fuel characteristics outside the predetermined range.

4. The fuel monitoring system of claim 1, wherein the deadman circuit is actuated by a control signal (16) wherein the sensed fuel characteristics sensed by the one or more sensors include at least one of a concentration of particulates and/or free water within the fuel flow.

5. The fuel monitoring system of claim 1, wherein the one or more sensors (3), (22), (8) are coupled in parallel to a primary fuel flow from the fuel supplier (1), the coupling of the one or more sensors (3), (22), (8) to the primary fuel flow being such that only a sample portion of the primary fuel flow passes through the one or more sensors (3), (22), (8).

6. The fuel monitoring system of claim 5, wherein the one or more sensors (3), (22), (8) includes a laser particle counter which measures the contamination of solid particulate and/or free water in the fuel flow.

7. The fuel monitoring system of claim 1, wherein the server arrangement (12) is connectable to a network and is remotely accessible over the network.

8. The fuel monitoring system of claim 1, wherein the server arrangement (12) includes an alarm block (13) that analyzes the data to determine if the fuel characteristics are within or outside a tolerable range, the server arrangement further includes a warning sending block (14) that sends a warning message to a user when the alarm block (13) determines that the fuel characteristics are outside a tolerable.

9. The fuel monitoring system of claim 1, wherein the data register-transmitter device (5) analyzes the data and determines if the fuel characteristics are within or outside a tolerable range, the system further includes a control signal to the deadman circuit (16) coupled to the data register-transmitter device (5) that operably stops the flow of fuel from the fuel supplier when the data register-transmitter device (5) determines that the fuel characteristics are outside a tolerable range.

10. The fuel monitoring system of claim 1, wherein the data insert block (9) or base station transmits the data to the server arrangement (12) upon the determination that the fuel characteristics are outside a tolerable range.

11. The fuel monitoring system of claim 1, wherein the data register-transmitter device (5) collects fuel flow data for individual operation cycles, each operation cycle beginning at the beginning of fuel flow being sensed and terminating upon sensing a stoppage of fuel flow.

12. The fuel monitoring system of claim 1 including a plurality of subsystems, the data register-transmitter of each subsystem (S1-Sn) being operably coupled to the base station (9), the base station (9) transmitting the data for each of the subsystems (S1-Sn) to the server arrangement (12).

13. The fuel monitoring system of claim 1, wherein the base station (9) is directly accessible such that data gathered by the one or more sensors (3), (22), (8) can be accessed by a user local to the base station (9).

14. A method of monitoring fuel quality comprising the steps of:
   dispensing a fuel flow from a fuel supplier;
   monitoring fuel characteristics of the fuel flow to generate fuel characteristics data;
   gathering the fuel characteristics data;
   transmitting the fuel characteristics data to a data register-transmitter;
   analyzing the fuel characteristics data to determine if it is within a tolerable range;
   stopping the fuel flow from the fuel supplier by using a deadman circuit proximate to the fuel supplier upon sensing of fuel characteristics outside a predetermined range range; and
   communicating a signal to the deadman circuit that can override contrary control by an operator.

15. The method of claim 14, wherein the step of monitoring the fuel characteristics includes continuously monitoring the fuel characteristics over an entire operation cycle and the step of analyzing occurs continuously over the entire operation cycle.

16. The method of claim 15 further comprising the step of automatically interrupting the fuel flow when the fuel characteristics are determined to be outside of the tolerable range.

17. The method of claim 15 further including the step of transmitting the fuel characteristics data to a data insert block or base station which will transmit data to a server arrangement being remote from the location where the step of monitoring is being performed and storing the fuel characteristics data on the server arrangement.

18. The method of claim 17, further including the step of remotely accessing the fuel characteristics stored on the server arrangement.

19. The method of claim 15, further including the step of dispatching a warning message to a user when the fuel characteristics are determined to be outside of the tolerable range.

* * * * *